US005179096A

United States Patent [19]

Gentilini et al.

[11] Patent Number: 5,179,096

[45] Date of Patent: Jan. 12, 1993

[54] THERAPEUTIC APPLICATION OF FLOUROQUINOLONE DERIVATIVES

[75] Inventors: Marc Gentilini, Briis Sous Forge; Anne Guyot; Michel Rosenheim, both of Paris, all of France

[73] Assignee: Rhone-Poulenc Sante, France

[21] Appl. No.: 625,408

[22] Filed: Dec. 11, 1990

[30] Foreign Application Priority Data

Dec. 11, 1989 [FR] France ................................ 89 16324

[51] Int. Cl.[5] ............................................ A61K 31/495

[52] U.S. Cl. ..................................................... 514/253

[58] Field of Search ................................ 514/255, 253

[56] References Cited

U.S. PATENT DOCUMENTS

| | | | |
|---|---|---|---|
| 4,292,317 | 9/1981 | Pesson | 544/363 |
| 4,382,892 | 5/1983 | Hayakawa et al. | 260/243.3 |
| 4,398,029 | 8/1983 | Irikura et al. | 544/363 |
| 4,448,962 | 5/1984 | Irikura et al. | 544/362 |
| 4,528,287 | 7/1985 | Itoh et al. | 544/254 |
| 4,551,456 | 11/1985 | Katz | 514/254 |
| 4,620,007 | 10/1986 | Grohe et al. | 546/156 |
| 4,670,444 | 6/1987 | Grohe et al. | 514/300 |
| 4,730,000 | 3/1988 | Chu | 514/254 |
| 4,772,605 | 9/1988 | Naik et al. | 514/254 |
| 4,774,246 | 9/1988 | Chu | 514/254 |
| 4,844,902 | 7/1989 | Grohe | 514/254 |
| 4,978,661 | 12/1990 | Caruso | 514/254 |

FOREIGN PATENT DOCUMENTS

| | | | |
|---|---|---|---|
| 206283 | 12/1986 | European Pat. Off. | 514/254 |
| 310849 | 4/1989 | European Pat. Off. | 514/294 |

OTHER PUBLICATIONS

Letters to nature, Ribosomal RNA sequence shows *Pneumocystis carinii* to be a member of the Fungi, Edman et al., Nature vol. 334, Aug. 1988.

European Search Report dated Aug. 28, 1990.

Derwent Abstract of U.S. Pat. No. 4,850,993.

Derwent Abstract of U.S. Pat. No. 4,853,225.

*Primary Examiner*—Allen J. Robinson

*Attorney, Agent, or Firm*—Morgan & Finnegan

[57] ABSTRACT

Application of fluoroqinolone derivatives of general formula (I) is taught, in which $R_1$ is alkyl (1 to 4C), fluoroethyl, cyclopropyl or difluorophenyl, $R_2$,$R_3$ and $R_4$ are identical or different and represent hydrogen atoms or methyl radicals, X is N or a group $=CR_6$ in which $R_6$ is a hydrogen or fluorine atom, or alternatively $R_6$ with $R_1$ and the atoms to which they are attached forms a six-membered heterocycle substituted with a methyl radical and containing an oxygen atom, and $R_5$ is a hydrogen atom, or represents an amino radical if $R_6$ is a fluorine atom, as well as of their salts, for obtaining a medicinal product intended for the preventive and/or curative treatment of pneumocystosis.

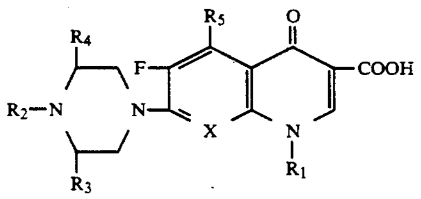

(I)

4 Claims, No Drawings

THERAPEUTIC APPLICATION OF FLOUROQUINOLONE DERIVATIVES

FIELD OF THE INVENTION

The present invention relates to a novel therapeutic application of the fluoroquinolone derivatives of general formula:

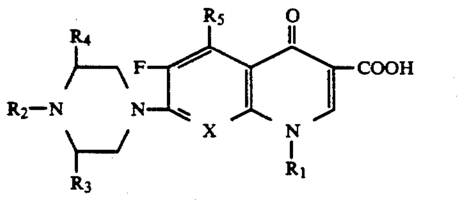

(I)

in which $R_1$ is an alkyl radical containing 1 to 4 carbon atoms or a fluoroethyl, cyclopropyl or difluorophenyl radical, $R_2$, $R_3$ and $R_4$ are identical or different and represent hydrogen atoms or methyl radicals, X represents a nitrogen atom or a group $=CR_6-$ in which $R_6$ is a hydrogen or fluorine atom, or alternatively $R_6$ with the radical $R_1$ and the atoms to which they are attached forms a six-membered heterocycle substituted with a methyl radical and optionally containing an oxygen atom, and $R_5$ is a hydrogen atom, or can represent an amino radical if $R_6$ is a fluorine atom, as well as their salts.

BACKGROUND OF THE INVENTION

The fluoroquinolone derivatives which form the subject of the present invention are widely known for their antimicrobial activity:

BE 870,576; U.S. Pat. No. 4,448,962, DE 3,142,854; EP 47,005; EP 206,283; BE 887,574; EP 221,463; EP 140,116; EP 131,839; EP 154,780; EP 78,362; EP 310,849.

Pneumocystis carinii is a ubiquitous microorganism capable of infecting many mammals.

In particular, in immunosuppressed humans, it is the source of severe hypoxaemia-inducing pneumonia, which is fatal in the absence of treatment.

Pneumonia caused by *Pneumocystis carinii* occurs in subjects such as premature infants or those suffering from a severe chronic disease, and older children or adults suffering from cancer or from hematological malignancies (leukosis, Hodgkin's disease) subjected to prolonged corticoid therapy or to an immunosuppressive treatment. Pneumonia caused by *Pneumocystis carinii* is, in effect, the commonest opportunistic infection of AIDS and is responsible for a high mortality rate in patients suffering from this disease.

DESCRIPTION OF THE INVENTION

It has been found that the fluoroquinolones of general formula (I), as well as their salts, possess an especially advantageous anti-Pneumocystis activity, and are thus entirely suitable for the preparation of a medicinal product intended for the preventive and/or treating of pneumocystosis of man and/or of animals.

Among the products of general formula (I), the products mentioned below are the preferred products: pefloxacin, enoxacin, norfloxacin, ofloxacin, ciprofloxacin, sparfloxacin, fleroxacin, lomefloxacin or temafloxacin.

The activity was demonstrated by the following test:

ACTIVITY AGAINST PNEUMOCYSTOSIS OF RATS

First Series of Trials

Rats weighing 200 to 250 g, immunosuppressed by two subcutaneous injections per week of hydrocortisone acetate (25 mg) and a protein-poor diet, are used.

Some rats additionally receive doxycycline (10 mg) subcutaneously twice weekly, so as to prevent the occurrence of infections other than pneumocystosis.

After two weeks of immunosuppression, the existence of a progressive pneumocystosis is verified by sacrificing some rats and counting the Pneumocystis present per gram of lung.

The products tested for their anti-Pneumocystis activity are dissolved in isotonic phosphate buffer at the desired concentration. They are administered intraperitoneally for two weeks.

Two groups of control animals are formed:

1/—immunosuppressed rats receiving doxycycline throughout the study period (four weeks), 2/—immunosuppressed rats receiving doxycycline only during the first two weeks of the study.

Another group of immunosuppressed rats, receiving doxycycline during the first two weeks of the study, receives the combination trimethoprim (40 mg/kg)/sulphamethoxazole (200 mg/kg) subcutaneously twice weekly during the last two weeks of the study.

Two groups of animals are treated with the product under study; they comprise immunosuppressed rats receiving doxycycline only during the first two weeks of the study, and then:

1/—the product under study (50 mg/kg) twice daily intraperitoneally during 14 days;

2/—the product under study (100 mg/kg) twice daily intraperitoneally during 14 days.

At the end of the four weeks, all the rats are sacrificed, the lungs are removed and the *Pneumocystis carinii* are counted.

RESULTS

The results obtained appear in Table I below.

At autopsy the lungs of the control animals of the 1st and 2nd groups were brownish-grey with broad oedematous areas. In contrast, those of the animals treated with the test product and with the trimethoprim/sulphamethoxazole combination (3rd control group) were pink and showed no pathological sign. The mean lung weights do not differ and are lower than those of the control animals.

Number of *Pneumocystis carinii:*

The control rats of groups 1 and 2 had a mean of $3.7\times10^7$ and $2.6\times10^7$ Pneumocystis per lung.

The animals treated with the test product had a mean of $1.3\times10^5$ Pneumocystis (50 mg/kg) and $8.9\times10^4$ Pneumocystis (100 mg/kg), respectively, per lung.

These values are very close to those obtained following treatment with the trimethoprim/sulphamethoxazole combination ($2.4\times10^4$ Pneumocystis).

CONCLUSION

The treatment with 50 mg/kg is especially effective.

SECOND SERIES OF TRIALS

In another series of trials, the control group consists of immunosuppressed rats receiving doxycycline (10 mg) subcutaneously twice weekly throughout the trial period (4 weeks).

Another group of immunosuppressed rats receives the combination trimethoprim (40 mg/kg)/suphamethoxazole (200 mg/kg) subcutaneously twice weekly from the start of immunosuppression.

The products under study are administered orally to immunosuppressed rats on the basis of 100 mg/kg 3 times weekly. The action of pefloxacin, temafloxacin and ofloxacin is studied.

After 4 weeks of immunosuppression, all the animals are sacrificed and the intrapulmonary Pneumocystis carinii are quantified.

RESULTS

The results obtained appear in Table II below.

Pefloxacin, temafloxacin and ofloxacin administered orally produce a decrease in the number of *Pneumocystis carinii.* compositions will be adapted to the particular case of the digestive tract of the immunosuppressed subjects.

As solid compositions for oral administration, tablets, pills, hard gelatin capsules, powders or granules may be used. In these compositions, the active product according to the invention is mixed with one or more inert diluents or adjuvants such as sucrose, lactose or starch. These compositions may comprise substances other than diluents, e.g. a lubricant such as magnesium stearate.

As liquid compositions for oral administration, solutions which are pharmaceutically acceptable, suspensions, emulsions, syrups and elixirs containing inert diluents such as water or liquid paraffin may be used. These compositions may also comprise substances other than diluents, e.g. wetting, sweetening or flavoring products.

The compositions for parenteral administration can be sterile solutions, aqueous or non-aqueous, suspensions or emulsions. As a solvent or vehicle, propylene glycol, a polyethylene glycol, vegetable oils, especially olive oil, and injectable organic esters, e.g. ethyl oleate, may be employed. These compositions can also contain adjuvants, especially wetting, tonicity, emulsifying, dispersant and stabilizing agents. The sterilization may be carried out in several ways, e.g. using a bacteriological filter, by irradiation or by heating. They may also be prepared in the form of sterile solid compositions which can be dissolved at the time of use in sterile water or any other sterile injectable medium.

TABLE I

ACTIVITY AGAINST MURINE PNEUMOCYSTOSIS

| | 1st control group + doxycyline (4 weeks) (6 rats) | 2nd control group + doxycyline (2 weeks) (4 rats) | Pefloxacin 50 mg/kg i.p. (5 rats) | Pefloxacin 100 mg/kg i.p. (5 rats) | Group receiving trimethoprim/ sulphamethoxazole 40/200 mg/kg s.c. (5 rats) |
|---|---|---|---|---|---|
| Initial weight (g) | 241 ± 17 | 238 ± 15 | 237 ± 12 | 238 ± 12 | 232 ± 8 |
| Weight + 4 weeks | 145 ± 16 | 147 ± 9 | 164 ± 6 | 163 ± 6 | 177 ± 10 |
| Rats dead | 3 | 0 | 0 | 2 | 1 (yeast) |
| Rats sacrificed | 3 | 4 | 5 | 3 | 4 |
| Lung weight (g) | 144 ± 0.31 | 1.36 ± 0.28 | 0.95 ± 0.04 | 0.86 ± 0.04 | 1.00 ± 0.15 |
| Number of Pneumocystis/g of lung | $3 \times 10^7 \pm 1.7 \times 10^7$ | $1.7 \times 10^7 \pm 2.4 \times 10^7$ | $1.4 \times 10^5 \pm 1 \times 10^5$ | $9.8 \times 10^4 \pm 12 \times 10^4$ | $2.3 \times 10^4 \pm 2.9 \times 10^4$ |
| Number of Pneumocystis per lung | $3.7 \times 10^7 \pm 2.1 \times 10^7$ | $2.6 \times 10^7 \pm 2.8 \times 10^7$ | $1.3 \times 10^5 \pm 1 \times 10^5$ | $8.9 \times 10^4 \pm 10 \times 10^4$ | $2.4 \times 10^4 \pm 2.8 \times 10^4$ |

After the first two weeks of immunosuppression, 3 rats were sacrificed: Number of Pneumocystis = $2 \times 10^6$/g of lung.

TABLE II

ACTIVITY AGAINST MURINE PNEUMOCYSTOSIS

| | Control group + doxycyline (4 weeks) (15 rats) | Pefloxacin 100 mg/kg p.o. (5 rats) | Temafloxacin 100 mg/kg p.o. (5 rats) | Ofloxacin 100 mg/kg p.o. (5 rats) | Group receiving trimethoprim/ sulphamethoxazole. 40/200 mg/kg s.c. (10 rats) |
|---|---|---|---|---|---|
| Initial weight (g) | 223 ± 18 | 237 ± 13 | 210 ± 6 | 236 ± 9 | 237 ± 14 |
| Weight + 4 weeks | 164 ± 22 | 183 ± 18 | 160 ± 12 | 205 ± 25 | 178 ± 11 |
| Rats dead | 2 | 0 | 0 | 0 | 1 |
| Rats sacrificed | 13 | 5 | 5 | 5 | 9 |
| Number of Pneumocystis/g of lung | $4.8 \times 10^6$<br>$2.1 \times 10^6 - 1.1 \times 10^7$ | $8.0 \times 10^3$<br>$3.0 \times 10^2 - 2.1 \times 10^5$ | $6.1 \times 10^5$<br>$2.1 \times 10^5 - 1.8 \times 10^6$ | $7.9 \times 10^5$<br>$1.4 \times 10^5 - 4.4 \times 10^6$ | $2.0 \times 10^3$<br>$1.0 \times 10^3 - 3.3 \times 10^3$ |

The present invention relates to the production of a medicinal product containing at least one product of general formula (I), optionally in salt form, in the pure state or in the form of a pharmaceutical composition in combination with one or more compatible diluents or adjuvants.

These compositions may be used orally, parenterally or as aerosols.

The compositions may be used for the purposes of cure or of prevention in subjects exhibiting an immunodeficiency and/or infected with *Pneumocystis carinii* and/or possessing a risk of contamination with *Pneumocystis carinii.* Naturally, the constitution of these The compositions intended for use in the form of liquid aerosols can be stable sterile solutions or solid compositions dissolved at the time of use in pyrogen-free sterile water, saline or any other pharmaceutically acceptable vehicle.

The aerosols can also be dry aerosols intended for direct inhalation, in which the finely divided active principle is combined with a water-soluble solid diluent or vehicle having a particle size of 30 to 80 microns, such as, e.g., dextran, mannitol or lactose.

In human therapy, the doctor will determine the dosage he considers most suitable in accordance with a preventive or curative treatment, in accordance with the age, weight, degree of infection and other factors specific to the subject to be treated. In general, the doses are between 1 and 5 g per day orally for an adult.

The examples which follow illustrate compositions according to the invention intended for the treatment of pneumocystosis:

EXAMPLE A

Tablets are prepared containing a 400-mg dose and having the following composition:

Pefloxacin in the form of a mesylate dihydrate: 400 mg

Excipient:

core: wheat starch, gelatin, talc, magnesium stearate, sodium carboxymethylstarch q.s. one core;

coating: hydroxypropylmethylcellulose, ethylcellulose, dibutyl sebacate, titanium oxide, talc, polyoxyethylene glycol 6,000.

EXAMPLE B

Tablets are prepared containing an 800-mg dose and having the following composition:

Pefloxacin in the form of a mesylate dihydrate: 800 mg

Excipient:

core: wheat starch, gelatin, talc, magnesium stearate, sodium carboxymethylstarch q.s. one core;

coating: hydroxypropylmethylcellulose, ethylcellulose, dibutyl sebacate, titanium oxide, talc, polyoxyethylene glycol 6,000.

The present invention also relates to compositions for preventive or curative veterinary use against pneumocystosis:

The compositions for veterinary use may be used in the various injectable dosage forms described above for administration in man. They can also be animal feeds or concentrated mixtures intended for animal feeding, containing a sufficient quantity of the derivative of general formula (I). More specifically, they can take the form of water-soluble powders to be mixed with the feed.

Generally speaking, the dosage to be employed will be that which is most suitable in accordance with the animal's weight, the degree of injection and other specific factors which may be involved, it being understood that the appropriate dose for producing an effect can vary within fairly wide limits.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A method intended for the treatment or prevention of pneumocystosis, comprising administering an effective amount of a product belonging to the fluoroquinolone class of formula:

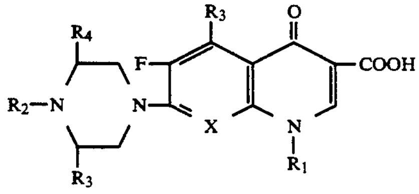

in which $R_1$ is an alkyl radical containing 1 to 4 carbon atoms, $R_2$, $R_3$ and $R_4$ are identical or different and represent hydrogen atoms or methyl radicals, X represents a group $=CR_4-$ in which $R_6$ is a hydrogen or fluorine atom, and $R_5$ is a hydrogen atom, or its salts to a mammal host in need thereof.

2. A method according to claim 1, intended for the treatment or prevention of pneumocystosis, wherein a product is administered belonging to the fluoroquinolone class, selected from pefloxacin, enoxacin, norfloxacin, ofloxacin, ciprofloxacin, sparfloxacin, fleroxacin, lomefloxacin or temafloxacin, or their salts.

3. A method according to claim 1, intended for the treatment or prevention of pneumocystosis, wherein a product is administered belonging to the fluoroquinolone class, selected from pefloxacin, ofloxacin or temafloxacin, or their salts.

4. A method according to claim 1, intended for the treatment or prevention of pneumocystosis in animals.

* * * * *